US007163538B2

United States Patent
Altarac et al.

(10) Patent No.: US 7,163,538 B2
(45) Date of Patent: Jan. 16, 2007

(54) POSTERIOR ROD SYSTEM

(75) Inventors: Moti Altarac, Aliso Viejo, CA (US); Philip A. Mellinger, Ladera Ranch, CA (US)

(73) Assignee: Cross Medical Products, Inc., Irvine, CA (US)

( * ) Notice: Subject to any disclaimer, the term of this patent is extended or adjusted under 35 U.S.C. 154(b) by 158 days.

(21) Appl. No.: 10/361,195

(22) Filed: Feb. 7, 2003

(65) Prior Publication Data

US 2003/0163133 A1   Aug. 28, 2003

Related U.S. Application Data

(60) Provisional application No. 60/356,996, filed on Feb. 13, 2002.

(51) Int. Cl.
*A61B 17/56* (2006.01)
*B25B 1/10* (2006.01)

(52) U.S. Cl. .................................................... 606/61
(58) Field of Classification Search ................ 606/61, 606/69, 60, 70, 71, 72, 73; 623/17.14, 20.22, 623/21.16, 23.4
See application file for complete search history.

(56) References Cited

U.S. PATENT DOCUMENTS

| | | | | |
|---|---|---|---|---|
| 2,190,585 A | * | 2/1940 | Rhinevault ................. 269/249 |
| 4,231,672 A | * | 11/1980 | Blanpain et al. ............... 403/62 |
| 5,591,166 A | * | 1/1997 | Bernhardt et al. ............. 606/61 |
| 5,628,740 A | * | 5/1997 | Mullane ....................... 606/61 |
| 5,733,286 A | * | 3/1998 | Errico et al. .................. 606/61 |
| 5,735,851 A | * | 4/1998 | Errico et al. .................. 606/61 |
| 5,800,435 A | * | 9/1998 | Errico et al. .................. 606/61 |
| 6,267,765 B1 | * | 7/2001 | Taylor et al. ................. 606/61 |
| 6,554,834 B1 | * | 4/2003 | Crozet et al. ................. 606/65 |
| 6,623,485 B1 | * | 9/2003 | Doubler et al. ............... 606/61 |

* cited by examiner

*Primary Examiner*—Pedro Philogene
(74) *Attorney, Agent, or Firm*—Hudak, Shunk & Farine Co. LPA

(57) ABSTRACT

The invention provides a rod assembly for implantation into the spine which includes a bone anchor assembly providing two points of angulation for the connection between the point of fixation and the rod. Further, the distance of offset between the point of fixation and the rod can be varied. The invention uses a bone screw having a pronged cage with a recess that accommodates the head of a post member. The cage can be tightened around the head by the camming surfaces of a locking cap that is drawn down around the compressible cage as the head is screwed upward in the recess by the engagement of the threads of the post by a locking nut. Further, the locking cap has a slotted bushing that is positionable in the elongated slot of a rod connector member. The locking nut includes an external taper that expands the bushing outward to lock it into position in the slot. In a further embodiment, the head has an internal hollow that receives a spindle journaled in a cavity in the recess to limit the amount of play in the assembly prior to tightening.

5 Claims, 2 Drawing Sheets

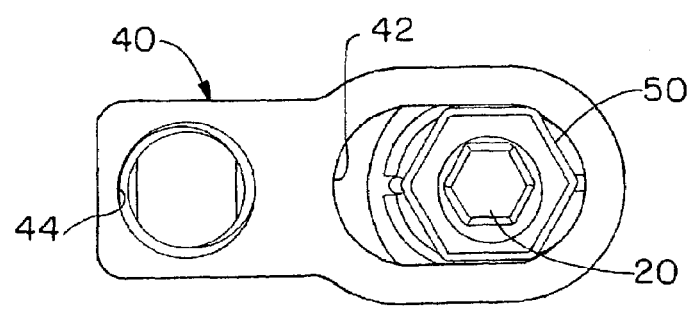
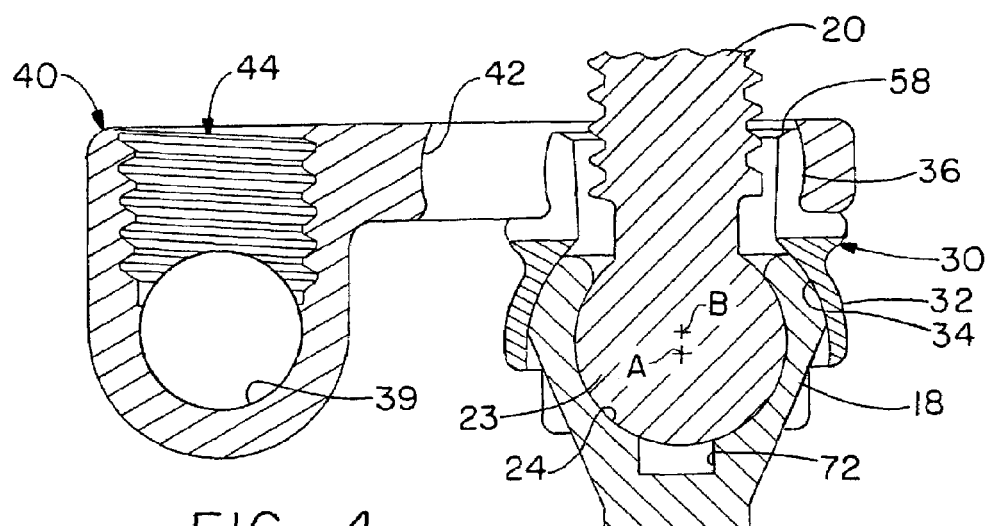
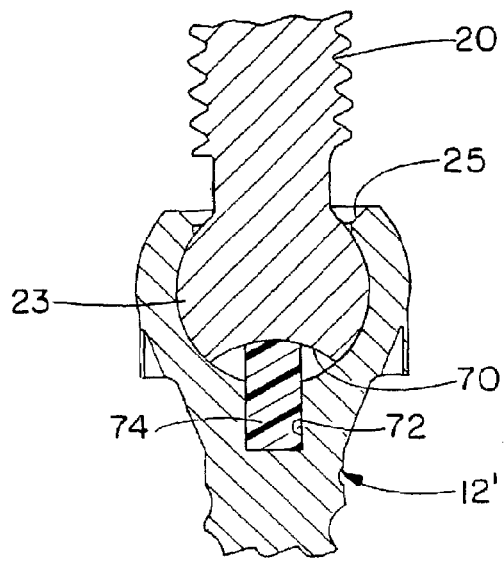

POSTERIOR ROD SYSTEM

This patent application is based upon U.S. Provisional Application Ser. No. 60/356,996, filed Feb. 13, 2002

The invention relates to an implant for the spine. In particular, the invention relates to a construct based on a rod which is held in a posterior relation to the spine using a multi-component bone anchor that includes multiple joints in order to achieve multiple degrees of freedom that can when desired be locked in a particular axial alignment.

BACKGROUND OF THE INVENTION

Constructs have been designed for some time for implantation in the spine which generally include a series of bone fasteners, such as hooks or screws, that are secured to the vertebrae, and which are used to hold stabilizer means such as a rod or plate that spans several vertebrae for stabilization, fixation, and/or for alignment of the vertebrae.

Typically, a spinal rod assembly includes two sets of rods that are fixed to adjacent vertebrae on either side of the spinous process to span a section of spine. The bone anchors may include a number of fixation means, such as screws or hooks, which are used for fixation to the spine, and anchor means, such as rod anchors that includes means to secure the rod to the fixation means. In some systems these component parts are a single integral unit, while other systems utilize a number of assembled components such as for the anchor portion of the assembly.

There are a number of considerations which go into the design of the assembly. The constructs need to be relatively easy to assembly, to be safe for the area of implantation, to provide for flexibility of use to accommodate a number of different indications for implantation and for variations in individuals who require their use, to be strong, yet minimally invasive and low profile, to be useful for manipulation, as well as for the maintenance of the desired alignment of the spine.

SUMMARY OF THE INVENTION

The present invention provides a multi-component bone anchor for use primarily with a rod in any area of the spine. The anchor includes multiple joints in order to provide many degrees of freedom by providing two selectively variable axes of alignment for the fixation assembly which can however, be easily locked to form a solid (i.e. fixed) point of fixation in the bone.

The invention has a bone screw with a concavely rounded interior surface formed within a cage (i.e. a compressible open recess having a series of resilient prongs) that receives the convexly rounded exterior surface of a post member, preferably to form a ball and socket, or more preferably a partial ball and socket type cooperation to define the first variable axis of rotation. A locking cap cooperates with a screw rod connector to form the second point of rotation for the second axis. The inwardly curving inner surface of the locking cap is preferably slightly smaller (i.e. relative to normal tolerances) than the corresponding top tapering surface of the cage so that it may act as a camming surface against the outwardly tapering camming surface defined by the pronged portion of the cage. A locking nut is screwed onto the post to cause locking of both the locking cap in the screw rod connector and of the cage in the locking cap as the post is drawn upward. Thus, a single locking step causes both axes of rotation to become fixed to make the construct more rigid in the bone.

More specifically, the system includes a bone screw having a pronged cage that retains the rounded and preferably hemi-spherical head of a post member. The bottom of the post head has a concave recess or dimple that engages a resilient spindle member captured in a recess at the bottom of the cage. The spindle member biases the post member upward against the inside of the restraining prongs of the cage. The post head has an upper rounded camming surface that urges the prongs outward to allow the post to be snap fit into place in the cage for assembly and also as a locking mechanism. The interior surface of the cage is slightly smaller than the outer diameter of the post head to ensure a fit which can be locked in place by compression by the downward action of the locking cap. Also the outer surface of the cage prongs collectively taper outwardly along the vertical axis of the screw to form a camming surface with the tapered (i.e. conical or curved) interior recess of the locking cap. Again, the locking cap interior surface has a slight corresponding taper to cause the cage to be biased inward and downward against the top surface of the post head engagement member as the post is screwed upward in relation to the locking cap. The locking cap has a slotted bushing that engages an elongated slot in a screw rod connector, which may also have an interior curve which mates with an exterior curve of the bushing to allow movement transverse to the rod axis as well as optionally at a variable angle. The screw rod connector includes a channel or recess for the rod which allows it to be offset from the point of fixation. The amount of offset is determined by the position of the locking cap in the rod connector slot. A locking nut has a bottom portion along a through bore with interior threads and a tapered exterior surface which increases in diameter towards the top. The top portion is a slightly larger head which includes an exterior hex driving surface, such as a hexagon shape. The interior threads of the hex headed locking nut engage the exterior threads on the post head, upward of the post engagement member. As the locking nut is screwed downward on the post, the taper biases the slotted bushing of the locking cap outward to lock it into place within the rod-connector slot. The post engagement member is drawn upward and locked into position against the prongs of the screw cage, which are in turn captured between the engagement member and the interior recess of the locking cap. The top portion of the post also has an external hex in order to allow the system to be tightened by turning the nut relative to the post while the post is held in a fixed position. In some cases, the surgeon may even decide to refrain from tightly locking the nut against the post member in order to retain some of the play of the fixation assembly which still acts as a tether and to accept some of the loading of the rod.

The proposed product is unique in allowing multiple degrees of freedom prior to tightening. The angle of the post can be varied about a first center of rotation with respect to the screw. The angle of the screw can be varied about a second center of rotation with respect to the locking cap which is secured in the slot in the screw-rod connector. The location of the locking cap in the slot of the screw-rod connector can also be varied.

OBJECTS OF THE INVENTION

It is an object of the invention to provide a bone anchor assembly that allows multiple degrees of freedom within defined parameters during surgical implantation and assembly and subsequent locking with an easy mechanism. These degrees of freedom include one or more of a variable angle for the bone screw relative to the rod axis, a variable angle for the bone screw connector relative to the rod axis, a variable amount of offset relative to the rod axis, and a variable height of the screw rod connector through the amount of tightening. Moreover, the construct allows for multiple ranges of movement after assembly, but prior to tightening, where all of theses can be locked by a single locking or tightening mechanism.

BRIEF DESCRIPTION OF THE DRAWINGS

FIG. 3 is a top view of the assembly of FIG. 1;
FIG. 4 is a cross-section of the assembly taken along line 4—4 of FIG. 1;
and
FIG. 5 is a cross-section showing an alternative embodiment of the invention.

DETAILED DESCRIPTION OF THE INVENTION

Figure 1:
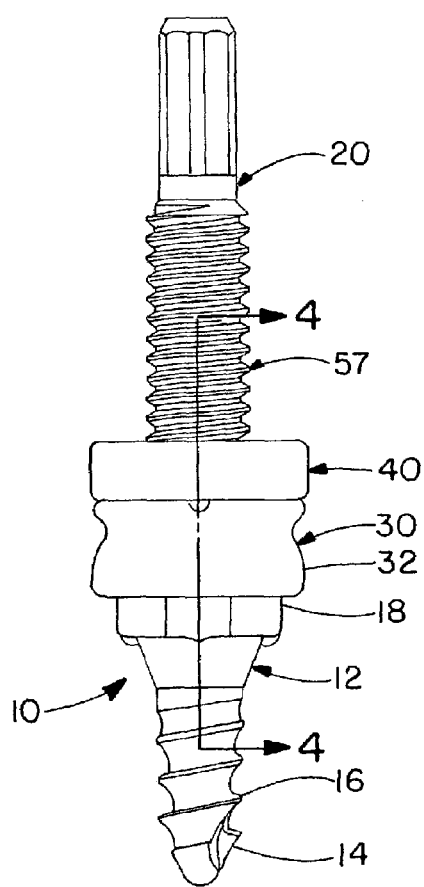
FIG. 1 is end view of the rod anchor assembly in accordance with the present invention.
Figure 2:
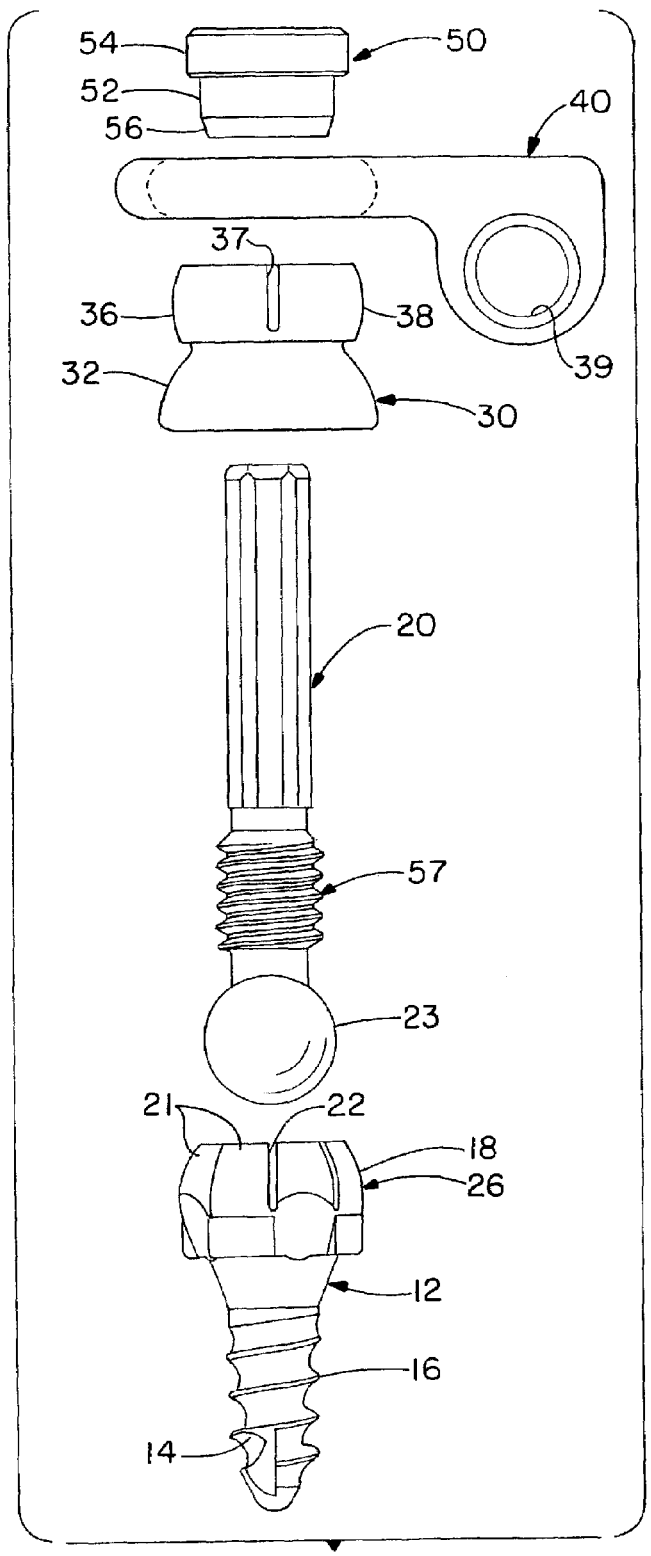
FIG. 2 is an exploded assembly view taken 90 degrees from FIG. 1.

The present invention provides a spinal implant assembly including a rod which is preferably not a threaded rod, and which is not shown, but which is held in position relative to the spine by a series of bone anchor assemblies as shown generally at 10 in FIG. 1. Specifically, the bone anchor assembly 10 includes a fixation member which comprises a bone screw 12 having a threaded lower portion which has a fluted area 14 and a suitable thread, such as a cancellous thread 16. The top of the bone screw 12 includes a receptacle such as a cage 18 for a post member 20. The cage comprises a plurality of resilient prongs 21 that are constructed by forming slots 22 in the top of the cage. At the top the prongs terminate to form a circular opening with a small bevel 25 to the top which is slightly smaller in diameter than the diameter of the engagement head 23. These prongs 21 can be deformed outward for the insertion of the engagement head of the screw, or inwardly for a compressive locking of the engagement head in a recess 24 which is shown as a spherical recess that receives the outwardly rounded engagement head 23 of the post member 20. Again the engagement head is shown as a sphere or in a second embodiment as a modified sphere. However, the top portion of the sphere of the engagement head 23 may preferably be slightly larger than the inner recess or cavity 24 of the cage.

The prongs also collectively have an outer surface 26 that tapers inward toward the central longitudinal axis of the screw and anchor assembly so that the bone screw has a pear type shape. A locking cap 30 has a through bore so that it can be fitted over the post member 20. The lower portion of the locking cap 30 forms a skirt 32 that has an upwardly tapered surface 34 on the inside. This can be a curving surface or a conical surface, but in any case, it is slightly smaller than the outer surface 26 of the prongs so as to enable a compressive contraction of the prongs 21 inward about the head of the engagement member 23. At the top, the locking cap includes a bushing 36 that may include a rounded surface 38 which mates with the elongated slot 42 in a flanged area of a screw rod connector 40. The slot may also include a corresponding inner rounded contour to allow the bone anchor assembly to be positioned at a variable angle, as well as at a variable distance of offset from the longitudinal axis of the stabilization rod. The rod is received in a channel 39 and secured in position by means such as a set screw which is received in the threaded recess 44 of the screw rod connector. The bushing 36 of the locking cap also includes a plurality of slots 37 that allow the bushing to be expanded outwardly against the sides of the slots 42 of the screw rod connector so that it may be locked in position.

The bone anchor assembly further includes a locking nut 50 having a tapered lower portion 52 and a torque receiving head 54 and an internal threaded throughbore. The lower portion 52 has a terminal bevel 56 that can be received in the terminal beveled opening 58 at the top of the bushing 36. The lower portion also includes a tapered portion 52 having an outer diameter which is slightly larger than the inner diameter of the bore on the inside of the bushing.

The post member includes a threaded portion 57 that mates with the internal threads on the locking nut 50. Specifically, before the assembly is locked, there are two points of axial angulation: A, which corresponds to the angulation of the post engagement head in the cage of the bone screw, and B, which corresponds to the angulation of the locking cap in the slot. However, both of these angles can be locked by the same locking mechanism. When the locking nut is tightened on the post member, the post member is drawn up against the inner recess of the cage which is drawn up in a tight contact with the locking cap. At the same time, the locking nut is drawn down into the bushing of the locking cap which expands to lock the cap in the slot of the screw rod connector.

The top of the post has a hexagon shape to allow it to be held during tightening. However, this top can subsequently be sheared off.

The embodiment shown in FIG. 5 is a preferred modification wherein the bottom portion of the engagement head 23 is contoured, to form a hollow recess 70 that is pressed upward by a resilient spindle member 72 which is captured in a cavity 74 in the cage. In this embodiment, the post member retains its ability to be variably angled in the cage, but it is biased outward against the cavity of the cage so that it is more apt to stay in a position in the cage before it is tightened (i.e. it is less apt to flop.)

A construct generally includes two rods on either side of the spinous process, and a series of bone anchor assemblies implanted in adjacent vertebrae. The assembly may also include other components, such as for example, plates, transverse connectors, cables, and hooks. The implants may be made of suitable implantable biocompatible materials, such as stainless steel and titanium, as well as ceramics, and composite materials.

While in accordance with the patent statutes the best mode and preferred embodiment have been set forth, the scope of the invention is not limited thereto, but rather by the scope of the attached claims.

What is claimed is:

1. A spinal implant comprising a rigid elongated stabilizer, and a plurality of bone anchor assemblies, said bone anchor assemblies comprising at least one assembly having a post member having a rounded head and fixation member defining an axis and having resilient prongs collectively having an outer convex camming surface and an inner surface which s into a recess which forms a socket about the axis, said socket having an inner area with a spindle and said socket retaining the head of the post member and having a mating interface so that the head is variably positionable within the recess, the at least one assembly further including a locking cap having an inner concave camming surface which forms a mating interface with the outer concave camming surface of the prongs such that the prongs are releasably compressible about the head to lock it into position, and a connector joining the post member to the stabilizer, the head further including a hollow that mates with the spindle whereby the head is biased by the spindle away from the inner area, and wherein the connector includes a slot and the locking cap includes a bushing and the bushing is received in the slot of the connector.

2. A spinal implant as set forth in claim 1 wherein the bushing includes means to lock the position of the bushing in the slot.

3. A spinal implant as set forth in claim 2 wherein the bushing includes a bore defining an internal surface mid the bushing has one or more slots and the means to lock the position of the bushing in the slot is a locking nut having an external taper which cooperates with the internal surface of the bore to expand the bushing.

4. A spinal implant as set forth in claim 3 wherein the post member has external treads which receive the locking nut.

5. A spinal rod assembly as set forth in claim 4 wherein the bushing is locked in the slot by tightening the locking cap on the threads of the post.

* * * * *

UNITED STATES PATENT AND TRADEMARK OFFICE
CERTIFICATE OF CORRECTION

PATENT NO. : 7,163,538 B2
APPLICATION NO. : 10/361195
DATED : January 16, 2007
INVENTOR(S) : Moti Altarac et al.

It is certified that error appears in the above-identified patent and that said Letters Patent is hereby corrected as shown below:

Col. 4, Line 59 Claim 1, line 7 please delete "s" and insert --opens-- therefor;

Col. 5, Line 11 Claim 3, line 2 please delete "mid" and insert --and--therefor; and Col. 6, Line 6 Claim 4, line 2, please delete "treads" and insert --threads--therefor Signed and Sealed this Seventeenth Day of April, 2007

JON W. DUDAS
*Director of the United States Patent and Trademark Office*